United States Patent
Chen et al.

(10) Patent No.: US 11,609,222 B2
(45) Date of Patent: Mar. 21, 2023

(54) WATER-SOIL INTERFACE PHYSIOCHEMICAL MONITORING APPARATUS AND RESERVOIR AREA HYDRO-FLUCTUATION BELT MONITORING SYSTEM BASED ON SAME

(71) Applicant: Nanjing Hydraulic Research Institute, Nanjing (CN)

(72) Inventors: Qiuwen Chen, Nanjing (CN); Dongsheng Liu, Nanjing (CN); Haoyu Zhu, Nanjing (CN); Jianyun Zhang, Nanjing (CN); Yuchen Chen, Nanjing (CN); Honghai Ma, Nanjing (CN); Yingxin Hong, Nanjing (CN)

(73) Assignee: Nanjing Hydraulic Research Institute, Nanjing (CN)

( * ) Notice: Subject to any disclaimer, the term of this patent is extended or adjusted under 35 U.S.C. 154(b) by 401 days.

(21) Appl. No.: 17/079,474

(22) Filed: Oct. 25, 2020

(65) Prior Publication Data
US 2021/0041412 A1    Feb. 11, 2021

(30) Foreign Application Priority Data

May 21, 2020    (CN) .......................... 202010433223.2

(51) Int. Cl.
*G01N 33/18*    (2006.01)
*G06F 1/3206*    (2019.01)
*H04W 84/18*    (2009.01)

(52) U.S. Cl.
CPC ....... *G01N 33/1886* (2013.01); *G06F 1/3206* (2013.01); *H04W 84/18* (2013.01)

(58) Field of Classification Search
CPC . G01N 33/1886; G06F 1/3206; H04W 84/18; G01D 21/02; G08C 17/02
See application file for complete search history.

(56) References Cited

U.S. PATENT DOCUMENTS 8,920,619 B2 * 12/2014 Salzer ................ G01N 33/1886
                                                                    204/403.01
10,006,897 B1 *  6/2018 Ensign ................... G01N 33/18
(Continued)

FOREIGN PATENT DOCUMENTS

| CN | 106908580 A | * | 6/2017 | |
| CN | 112268996 A | * | 1/2021 | ............. G01D 21/02 |
| CN | 113155203 A | * | 7/2021 | ............. G01D 21/02 |

*Primary Examiner* — Francis C Gray
(74) *Attorney, Agent, or Firm* — CBM Patent Consulting, LLC

(57) ABSTRACT

A water-soil interface physiochemical monitoring apparatus and a reservoir area hydro-fluctuation belt monitoring system based on the same. The water-soil interface physiochemical monitoring apparatus comprises a cylindrical shell, a conical head, a sensor data acquisition circuit, a sealing plug, and a plurality of sensor modules. One end of the cylindrical shell is in sealing connection with the conical head, and the other end is sealed by the sealing plug. The sensor modules are connected to the sensor data acquisition circuit, and are all located in the sealed space of the cylindrical shell. Each sensor module comprises a circuit board, a temperature sensor, a dissolved oxygen sensor and a conductivity sensor, which are combined together by casting using resin, and the temperature sensor, the dissolved oxygen sensor and the conductivity sensor are separately connected to the circuit board.

6 Claims, 4 Drawing Sheets

IA: Information Acquisition Apparatus; WTD: Wireless Transmission Device

(56) References Cited

U.S. PATENT DOCUMENTS

| | | | |
|---|---|---|---|
| 2003/0227394 A1* | 12/2003 | Rothgeb | A47L 15/4297 340/870.01 |
| 2016/0061796 A1* | 3/2016 | Miller | G01N 7/00 73/19.1 |
| 2019/0204287 A1* | 7/2019 | Chen | G01N 1/08 |

* cited by examiner

Front View

Left View

Top View

WATER-SOIL INTERFACE PHYSIOCHEMICAL MONITORING APPARATUS AND RESERVOIR AREA HYDRO-FLUCTUATION BELT MONITORING SYSTEM BASED ON SAME

This application claims priority to Chinese Patent Application Ser. No. CN202010433223.2 filed on 21 May 2020.

TECHNICAL FIELD

The present invention relates to environment monitoring technology, and in particular to a water-soil interface physiochemical monitoring apparatus and a reservoir area hydro-fluctuation belt monitoring system based on the same.

BACKGROUND

According to statistics, as of 2011, a total of about 16.7 million reservoirs of various types have been built worldwide, which is still increasing over time. The operation of a reservoir will cause periodic fluctuation of the water level in the reservoir area, and as a result, a vast flooding-drying area, a hydro-fluctuation belt, is formed in the reservoir area. The special hydrological process of the hydro-fluctuation belt makes the soil pore water and overlying water of the hydro-fluctuation belt exchange frequently, resulting in dynamic changes in substance concentration, physiochemical parameters and microbiological properties of the water-soil interface, which provides an important place for the biogeochemical reactions of nutritive salt accumulated in the reservoir. Understanding the long-term change of basic physiochemical parameters of water-soil interfaces at different depths in a hydro-fluctuation belt is the basis of revealing true facts about the biogeochemical reaction of the hydro-fluctuation belt. For a long time, the physiochemical properties of water-soil interfaces in reservoir areas have been mostly monitored by manpower. For the monitoring of deep water areas, the influence of water buoyancy and other factors often lead to uncertainty in measurement, and long-term monitoring usually takes a lot of time and labor. The continuous automatic monitoring of physiochemical properties of water-soil interfaces in reservoir areas has long been a big problem, particularly for deep water areas.

SUMMARY

Objective

To solve the problem existing in the prior art, the present invention provides a water-soil interface physiochemical monitoring apparatus and a reservoir area hydro-fluctuation belt monitoring system based on the same, which are particularly suitable for a hydro-fluctuation belt with dramatic water-level changes in a reservoir area. The monitoring apparatus can continuously monitor the physiochemical properties of the hydro-fluctuation belt interface. The reservoir area hydro-fluctuation belt monitoring system can remotely monitor the change of physiochemical properties at different depths of the hydro-fluctuation belt in the reservoir area. The present invention features efficient measuring process, and temporally flexible, real-time and continuous monitoring.

Technical Solution

The water-soil interface physiochemical monitoring apparatus disclosed herein comprises a cylindrical shell, a conical head, a sensor data acquisition circuit, a sealing plug, and a plurality of sensor modules. One end of the cylindrical shell is in sealing connection with the conical head, and the other end is sealed by the sealing plug. The sensor modules are connected to the sensor data acquisition circuit, and are all located in the sealed space of the cylindrical shell. Each sensor module comprises a circuit board, a temperature sensor, a dissolved oxygen sensor and a conductivity sensor, which are combined together by casting using resin, and the temperature sensor, the dissolved oxygen sensor and the conductivity sensor are separately connected to the circuit board; the cylindrical shell is provided with holes in 3 directions corresponding to a mounting position of each sensor module, such that probes of the temperature sensor, the dissolved oxygen sensor and the conductivity sensor of the corresponding sensor module are exposed to outside of the cylindrical shell via the holes.

The apparatus further comprises a status indicator lamp. The status indicator lamp is located outside the cylindrical shell, and is connected to the sensor data acquisition circuit through the sealing plug.

The apparatus further comprises a power supply and a memory module. The power supply and the memory module are located inside the cylindrical shell, the power supply powers the whole apparatus, and the memory module is connected to the sensor data acquisition circuit.

The apparatus further comprises an optical fiber and a power wire. Both the optical fiber and the power wire are inserted into the cylindrical shell through the sealing plug, and are connected to the sensor data acquisition circuit.

Furthermore, the distance between the holes corresponding to the adjacent sensor modules located at the uppermost two layers is 5 cm, and the distance between the holes corresponding to the other adjacent sensor modules is 10 cm.

The reservoir area hydro-fluctuation belt monitoring system disclosed herein comprises an information acquisition apparatus, a water level gauge, a wireless transmission system, a power supply system, an intelligent platform, and a plurality of the water-soil interface physiochemical monitoring apparatuses described above, wherein:

the water-soil interface physiochemical monitoring apparatuses are vertically inserted into different elevations of the hydro-fluctuation belt of the reservoir area, with the sensors facing the water area and the uppermost sensors located at the water-sediment interface;

the information acquisition apparatus comprises a memory module and an information processing module, and is installed on the shore, the information acquisition apparatus being connected to the water-soil interface physiochemical monitoring apparatuses through optical fibers and configured to control and monitor the monitoring apparatuses, adjust the monitoring frequencies of the monitoring apparatuses and the operating states of the sensors, and collect and back the data of the monitoring apparatuses up to the memory module;

the water level gauge is installed near the monitoring apparatuses and connected to the information acquisition apparatus, and is configured to monitor the water level fluctuation in the reservoir area, the frequency for water level information acquisition being consistent with the monitoring frequency of the monitoring apparatuses;

the wireless transmission system comprises a wireless transmission device, a server, and wireless serial port software, the wireless transmission device being connected to the information acquisition apparatus and sending data to the server through a wired or wireless network, and the wireless serial port software being configured for a user remotely accessing the data of the server and controlling the reservoir area hydro-fluctuation belt monitoring system through the intelligent platform;

the intelligent platform is connected to the wireless serial port software through a virtual serial port, and is configured to remotely access the operating states of the monitoring apparatuses and the water level gauge and the data in the information acquisition apparatus, compare changes in parameters at different positions and different sediment depths, and remotely adjust the monitoring frequencies of the monitoring apparatuses and the operating states of the sensors, for example, when the monitoring apparatuses operate abnormally, the information acquisition apparatus receives warning information and sends apparatus abnormality warning information to the intelligent platform via the wireless transmission system; in addition, the setting of data abnormality is allowed to warn the platform when the change of certain data in a certain period of time is greater than a certain constant (for example, the change of dissolved oxygen data is greater than 3 mg/L in five measurements); and the power supply system comprises a power supply and a solar panel, the power supply system being installed on the shore and configured to power the whole monitoring system.

Advantages

Compared with the prior art, the present invention has the following outstanding advantages:

(1) Automation: At present, manual on-site monitoring requires long-term measurement, and poses difficulties in the deep-water period and interference in measurement. By contrast, the present invention basically achieves automatic monitoring, directly result outputting, and operation state viewing via network, thus greatly improving the working efficiency;

(2) Continuity: The present invention implements real-time dynamic monitoring and displays the change of physiochemical properties of water-sediment interfaces of a hydro-fluctuation belt in a reservoir area in real time, which helps to enhance the understanding of the biogeochemical reaction mechanism of the hydro-fluctuation belt under the influence of the impounding and draining processes of the reservoir; and (3) Specificity: The present invention overcomes the problem of the great water level fluctuation in the hydro-fluctuation belt of the reservoir area, and the problem that the stratum structure cannot be observed by drilling because the impounding of the reservoir area generally requires a permeable layer as the shallow stratum and a natural or artificial weak permeable layer below.

DETAILED DESCRIPTION

Example 1

Figure 1:
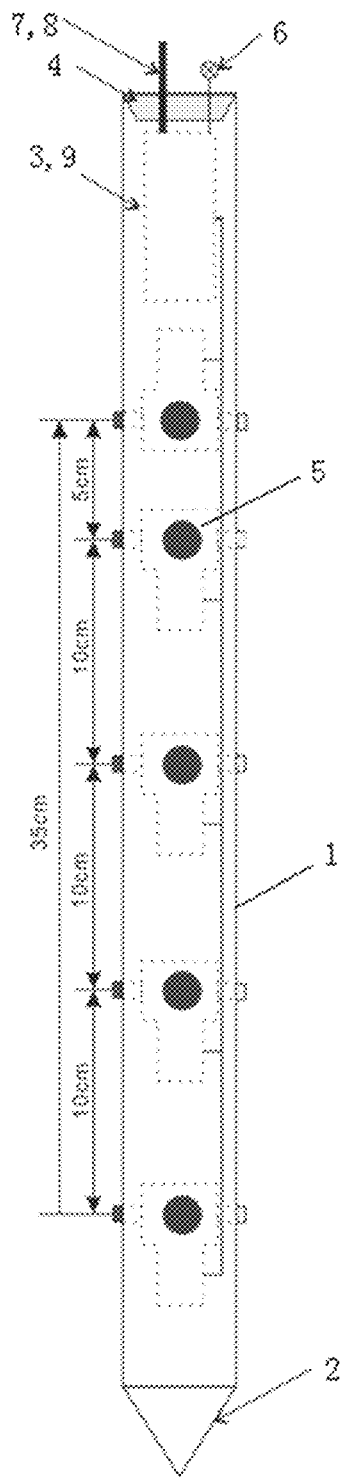
FIG. 1 is a structural schematic diagram of a water-soil interface physiochemical monitoring apparatus of the present invention.
Figure 2:
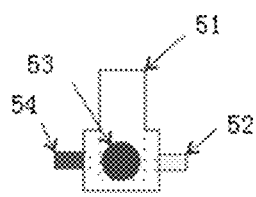
FIG. 2 is a structural schematic diagram of the sensor module in FIG. 1 according to the present invention.
Figure 2:
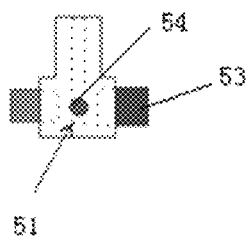
Figure 2:
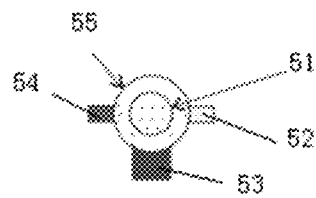

This example provides a water-soil interface physiochemical monitoring apparatus, as shown in FIG. 1, comprising a cylindrical shell 1, a conical head 2, a sensor data acquisition circuit 3, a sealing plug 4, and a plurality of sensor modules 5. The whole apparatus is 60 cm in length, 5 cm in outer diameter and 4.6 cm in inner diameter, and the conical body is 5 cm in length. The cylindrical shell 1 is a PVC tube, of which one end is in sealing connection with the conical head 2 with polystyrene filled in the seal, and the other end is sealed by the sealing plug 4. The sensor modules 5 are connected to the sensor data acquisition circuit 3, and are all located in the sealed space of the cylindrical shell 1. As shown in FIG. 2, each sensor module 5 comprises a circuit board 51, a temperature sensor 52, a dissolved oxygen sensor 53 and a conductivity sensor 54, which are combined together by casting using resin 55 for fixing and waterproofing, and the temperature sensor 52, the dissolved oxygen sensor 53 and the conductivity sensor 54 are separately connected to the circuit board 51. The cylindrical shell 1 is provided with holes in 3 directions corresponding to a mounting position of each sensor module 5, such that probes of the temperature sensor, dissolved oxygen sensor and conductivity sensor of the corresponding sensor module are exposed to outside of the cylindrical shell 1 via the holes. Specifically, the distance between the holes corresponding to the adjacent sensor modules located at the uppermost two layers is 5 cm, and the distance between the holes corresponding to the other adjacent sensor modules is 10 cm. The measuring range and precision of the sensors are as follows: the temperature sensor (−4° C. to 50° C., 0.1° C.); the dissolved oxygen sensor (0 to 25 mg/L, 0.1 mg/L, convertible into percentage); and the conductivity sensor (0 to 2000 μs/cm, 1 μs/cm). The apparatus is also provided with a status indicator lamp 6, which passes through and is located outside the cylindrical shell 1, and is connected to the sensor data acquisition circuit 3 through the sealing plug 4. Specifically, the status indicator lamp 6 is a light-emitting diode and has different colors and flashing frequencies for different statuses. The apparatus is connected to other apparatuses in a wired manner, thus further comprising a connecting optical fiber 7 and a connecting power wire 8, which are inserted into the cylindrical shell 1 through the sealing plug 4 and connected to the sensor data acquisition circuit 3. The apparatus further comprises a power supply and a memory module 9 located inside the cylindrical shell. The power supply powers the whole apparatus, and the memory module is connected to the sensor data acquisition circuit 3.

Figure 3:
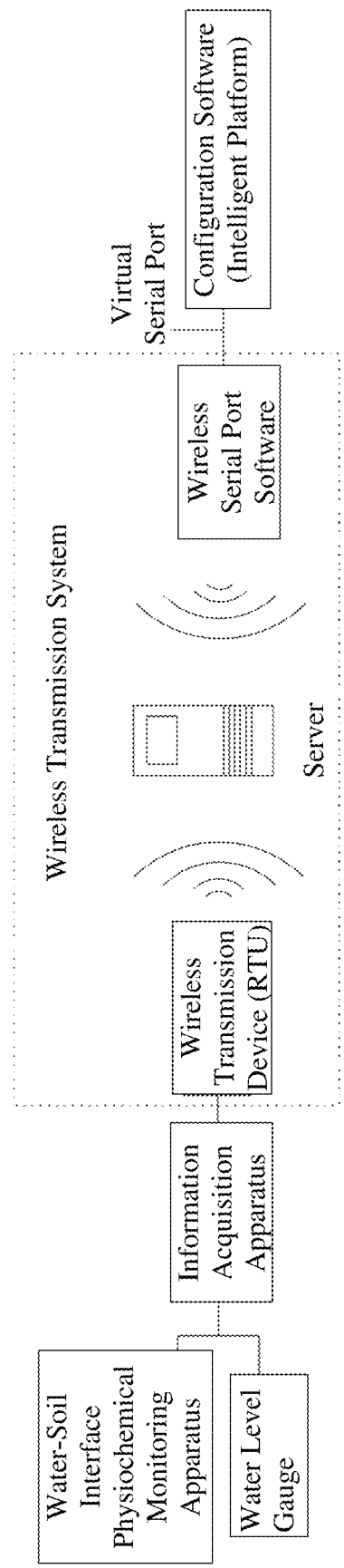
FIG. 3 is a structural schematic diagram of the reservoir area hydro-fluctuation belt monitoring system of the present invention.
Figure 4:
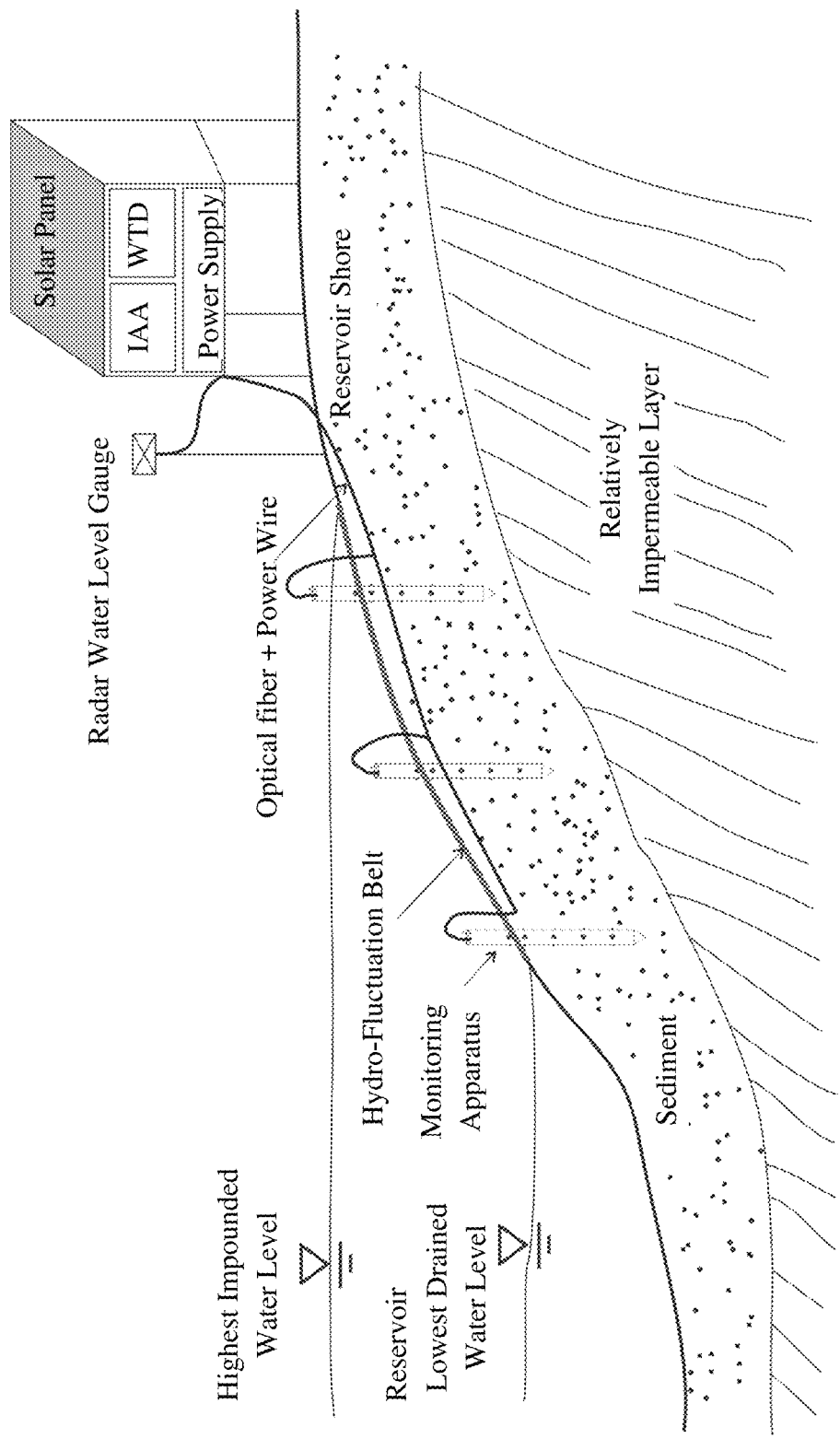
FIG. 4 is a schematic diagram of the arrangement of the reservoir area hydro-fluctuation belt monitoring system.

This example further provides a reservoir area hydro-fluctuation belt monitoring system, as shown in FIG. 3, which comprises an information acquisition apparatus, a water level gauge, a wireless transmission system, a power supply system, an intelligent platform, and a plurality of the water-soil interface physiochemical monitoring apparatuses described above. The water-soil interface physiochemical monitoring apparatuses are vertically inserted into different elevations of the hydro-fluctuation belt in a reservoir area. More specifically, the three sensors are vertically inserted at three elevations, facing the water area, and the uppermost sensors are just located at a water-sediment interface to measure the physiochemical properties of overlaying water. For example, as shown in FIG. 4, in an impounding and draining solution for a reservoir, the highest impounded water level and the lowest drained water level are respectively 55 m and 35 m. Thus the monitoring apparatuses are respectively arranged at the elevations of 40 m, 45 m and 50 m in the hydro-fluctuation belt (the density can be increased or decreased according to accuracy requirement or the "heat" of the geochemical reaction of the hydro-fluctuation belt). Specifically, the apparatuses should be installed during the drying period of the hydro-fluctuation belt. The status indicator lamp is red when the monitoring apparatus is electrified but is not measuring, green during normal monitoring, and red and flashing when the monitoring apparatus goes wrong. The power supply system comprises a power supply and a solar panel. The power supply system is installed on the shore and configured to power the whole monitoring system. The information acquisition apparatus, which may be connected to the monitoring apparatuses in a wired or wireless manner, comprises a memory module and an information processing module, and is configured to acquire and store the data of each sensor from all the water-soil interface physiochemical monitoring apparatuses into the memory device, control and monitor the monitoring apparatuses, adjust the monitoring frequencies of the monitoring apparatuses and the operating states of the sensors, collect and back the data of the monitoring apparatuses up to the memory module, and transmit the data to the intelligent platform via the wireless transmission system. The water level gauge, which is a radar water level gauge with a precision of 5 cm, is installed near the monitoring apparatuses and connected to the information acquisition apparatus, and is configured to monitor the water level fluctuation in the reservoir area. The frequency for water level information acquisition is consistent with the monitoring frequency of the monitoring apparatuses. The wireless transmission system comprises a wireless transmission device, a server, and wireless serial port software. The wireless transmission device is connected to the information acquisition apparatus and sends data to the server through a wired or wireless network, and the wireless serial port software is configured for a user remotely accessing the data of the server and controlling the reservoir area hydro-fluctuation belt monitoring system through the intelligent platform. The intelligent platform is connected to the wireless serial port software through a virtual serial port, and is configured to remotely access the operating states of the monitoring apparatuses and the water level gauge and the data in the information acquisition apparatus, compare changes in parameters at different positions and different sediment depths, and remotely adjust the monitoring frequencies of the monitoring apparatuses and the operating states of the sensors. During normal monitoring, the monitoring apparatuses transmit sensor data to the information acquisition apparatus via optical fibers, and the information acquisition apparatus transmits the sensor data and water level data to the intelligent platform via the wireless transmission system. When a monitoring apparatus operates abnormally, the monitoring apparatus immediately warns the information acquisition apparatus, and the status indicator lamp turns red at the same time, such that the position of the abnormal monitoring apparatus can be conveniently directly found in the field. The information acquisition apparatus sends the warning information to the intelligent platform via a RTU. In addition, the setting of data abnormality is allowed to warn the platform when the change of certain data between two measurements is greater than a certain constant (for example, the change of dissolved oxygen data is greater than 3 mg/L in two measurements). The monitoring time interval of the monitoring apparatuses and the water level gauge can be set artificially, and the default setting is 3 hours. In the monitoring apparatus list of the intelligent platform, operating states and real-time data of the monitoring apparatuses and the water level gauge can be directly viewed, and the historical data of a monitoring apparatus or the water level gauge can be checked or the data of all the monitoring apparatuses at different water levels can be compared as well.

Example 2

This example provides another water-soil interface physiochemical monitoring apparatus. The only difference between the apparatus and the terrain monitoring apparatus in Example 1 is that the apparatus is suitable for a shore zone with small water level fluctuation and a short monitoring period. The apparatus is connected to other apparatuses in a wireless manner, and therefore does not comprises an optical fiber and a power wire, but comprises a power supply and a wireless communication module located in the cylindrical shell. The power supply powers the whole apparatus, and the wireless communication module is connected to a sensor data acquisition circuit. Specifically, the wireless communication module may be any of GPRS, 3G, 4G, 5G, WIFI and Bluetooth.

This example further provides another reservoir area hydro-fluctuation belt monitoring system with the only difference from the system in Example 1 being: comprising water-soil interface physiochemical monitoring apparatuses described in this example.

What is claimed is:

1. A water-soil interface physiochemical monitoring apparatus, comprising a cylindrical shell, a conical head, a sensor data acquisition circuit, a sealing plug, and a plurality of sensor modules, wherein one end of the cylindrical shell is in sealing connection with the conical head, and the other end is sealed by the sealing plug; the sensor modules are connected to the sensor data acquisition circuit, and are all located in the sealed space of the cylindrical shell; each sensor module comprises a circuit board, a temperature sensor, a dissolved oxygen sensor and a conductivity sensor, which are combined together by casting using resin, and the temperature sensor, the dissolved oxygen sensor and the conductivity sensor are separately connected to the circuit board; the cylindrical shell is provided with holes in 3 directions corresponding to a mounting position of each sensor module, such that probes of the temperature sensor, the dissolved oxygen sensor and the conductivity sensor of the corresponding sensor module are exposed to outside of the cylindrical shell via the holes.

2. The water-soil interface physiochemical monitoring apparatus according to claim 1, further comprising a status indicator lamp, wherein the status indicator lamp is located outside the cylindrical shell, and is connected to the sensor data acquisition circuit through the sealing plug.

3. The water-soil interface physiochemical monitoring apparatus according to claim 1, further comprising a power supply and a memory module, wherein the power supply and the memory module are located inside the cylindrical shell, the power supply powers the whole apparatus, and the memory module is connected to the sensor data acquisition circuit.

4. The water-soil interface physiochemical monitoring apparatus according to claim 1, further comprising an optical fiber and a power wire, wherein both the optical fiber and the power wire are inserted into the cylindrical shell through the sealing plug, and are connected to the sensor data acquisition circuit.

5. The water-soil interface physiochemical monitoring apparatus according to claim 1, wherein the distance between the holes corresponding to the adjacent sensor modules located at the uppermost two layers is 5 cm, and the distance between the holes corresponding to the other adjacent sensor modules is 10 cm.

6. A reservoir area hydro-fluctuation belt monitoring system, comprising an information acquisition apparatus, a water level gauge, a wireless transmission system, a power supply system, an intelligent platform, and a plurality of water-soil interface physiochemical monitoring apparatuses according to claim 1,
wherein:
the water-soil interface physiochemical monitoring apparatuses are vertically inserted into different elevations of the hydro-fluctuation belt of the reservoir area, with the sensors facing the water area and the uppermost sensors located at the water-sediment interface;

the information acquisition apparatus comprises a memory module and an information processing module, and is installed on the shore, the information acquisition apparatus being connected to the water-soil interface physiochemical monitoring apparatuses through optical fibers and configured to control and monitor the monitoring apparatuses, adjust the monitoring frequencies of the monitoring apparatuses and the operating states of the sensors, and collect and back the data of the monitoring apparatuses up to the memory module;

the water level gauge is installed near the monitoring apparatuses and connected to the information acquisition apparatus, and is configured to monitor the water level fluctuation in the reservoir area, the frequency for water level information acquisition being consistent with the monitoring frequency of the monitoring apparatuses;

the wireless transmission system comprises a wireless transmission device, a server, and wireless serial port software, the wireless transmission device being connected to the information acquisition apparatus and sending data to the server through a wired or wireless network, and the wireless serial port software being configured for a user remotely accessing the data of the server and controlling the reservoir area hydro-fluctuation belt monitoring system through the intelligent platform;

the intelligent platform is connected to the wireless serial port software through a virtual serial port, and is configured to remotely access the operating states of the monitoring apparatuses and the water level gauge and the data in the information acquisition apparatus, compare changes in parameters at different positions and different sediment depths, and remotely adjust the monitoring frequencies of the monitoring apparatuses and the operating states of the sensors; and the power supply system comprises a power supply and a solar panel, the power supply system being installed on the shore and configured to power the whole monitoring system.

\* \* \* \* \*